United States Patent [19]

Louiday

[11] Patent Number: 4,866,751
[45] Date of Patent: Sep. 12, 1989

[54] RADIOLOGICAL DEVICE OF THE PIVOTING TYPE

[75] Inventor: André E. Louiday, Le Peco, France

[73] Assignee: U.S. Philips Corporation, New York, N.Y.

[21] Appl. No.: 253,786

[22] Filed: Oct. 5, 1988

[30] Foreign Application Priority Data

Oct. 6, 1987 [FR] France .................................. 87 13771

[51] Int. Cl.[4] .............................................. H05G 1/02
[52] U.S. Cl. ..................................... 378/196; 378/195; 378/197; 378/209
[58] Field of Search ................ 378/193, 177, 195–198, 378/208, 209

[56] References Cited

U.S. PATENT DOCUMENTS 4,481,656 11/1984 Janssen et al. ....................... 378/196
4,653,083 3/1987 Rossi .................................... 378/197
4,741,015 4/1988 Charrier .............................. 378/197

FOREIGN PATENT DOCUMENTS 1262145 4/1961 France ................................. 378/196
56-155937 10/1981 Japan ................................... 378/197

Primary Examiner—Carolyn E. Fields
Assistant Examiner—Joseph A. Hynds
Attorney, Agent, or Firm—Thomas A. Briody; Jack E. Haken; Jack D. Slobod

[57] ABSTRACT

Radiological device of the pivoting type, comprising a fixed base (1), a longitudinal pivoting carriage (2) mounted on the base (1) and carrying, on the one hand longitudinally, a patient support panel (8) connected to the carriage by a patient support panel support, the panel support consisting of a bracket (3), the top horizontal beam (5) of which, which is mounted on an arm (6), forms a bridge for the passage of a practitioner.

3 Claims, 2 Drawing Sheets

RADIOLOGICAL DEVICE OF THE PIVOTING TYPE

The invention relates to a radiological device of the pivoting type, comprising a base, a longitudinal pivoting carriage mounted on the base and carrying, on the one hand longitudinally, a patient support panel connected to the carriage by a patient support panel support, and, on the other hand, an arck support equipped with an arck which itself carries an X-ray analysis system, composed of an X-ray source and of an X-ray receiver.

An example of a radiological device is given in U.S. Pat. No. 2,565,093. This patent describes a radiological device comprising a carriage and a patient support panel connected to the said carriage by means of a substantially horizontal support in such a manner as to provide, between the patient support panel and the carriage, a space which is sufficient for a practitioner to pass.

Currently, devices for radiodiagnostics are preferably used in surgery and permit alternately, on the one hand, a radiological analysis of a specified part of the human body and, on the other hand, the surgical treatment of this part, this taking place in dependence upon the requirements of the practitioners.

The radiological device described in the mentioned patent does not permit such an alternation and possesses disadvantages such as, for example, The space existing between the carriage and the patient support table is fixed;

the carriage must have a great length in order to be able to release a space between, on the one hand, the X-ray analysis arch which is then displaced at the end of the carriage and, on the other hand, the end part of the patient support panel;

in this position, the pivoting of the patient support panel is no longer possible, the X-ray analysis arch then coming into contact with the ground;

when the practitioner desires to use the X-ray analysis system during an exploratory operation or the surgical treatment, total access to the patient is no longer possible.

The subject of the invention is a radiological device which can be used simultaneously for radiodiagnostics and for surgery of the human body, it being possible for the monitoring or the exploration by X-ray analysis to be undertaken while having access to both sides of the patient spread out on the patient support panel, without obstruction or blockage.

It is characterized in that the panel support consists of a bracket, forming a solid unit with the pivoting carriage, fixed to one end of the said carriage and the top horizontal beam of which carries, at its free end, an arm transverse to th beam, this arm being equipped with an angle member carrying the patient support panel by one of its ends, the bracket and the arm forming a bridge for the passage of a practitioner.

The bracket placed at one end of the carriage permits the compensation of a part of the load of the X-ray analysis system, the balancing of the masses on both sides of the means of rotation of the carriage permits the reduction of the power of the motor, the function of which is the rotational drive of the said carriage.

The bridge formed by the patient support panel support offers a passage for access on the part of the practitioners on both sides of the patient during the use of the X-ray analysis system.

The pivoting carriage is of a length substantially equal to the length of the patient support panel.

The passage between the patient support panel and the carriage permits, by a cylindrical rotation of the arch about its central axis and a rotation of the arch support about its axis of rotation, the symmetrical reversal of the position of the X-ray source and of the tube to receive X-rays in relation to the patient support panel.

In a particular form of the invention, the beam is a slide in which slides a horizontal sliding member forming a solid unit with the arm; this permits the variation of the space existing between the pivoting carriage and the panel for the purpose of:

positioning the patient in relation to the X-ray analysis system, separating the patient from the analysis system, opening a large space around the patient.

Preferably, the arm is equipped with a slideway mounted on the angle member for a displacement of the patient support panel in planes perpendicular to the longitudinal axis of the arm.

By its movement, the slideway permits the placing of the patient correctly in relation to the X-ray analysis system and the regulation of the height of the panel in relation to the ground, in such a manner that the practitioners can operate under good conditions.

The description given hereinbelow, with reference to the accompanying drawings, the whole being given by way of non-limiting example, will provide a good understanding of how the invention can be implemented.

Figure 1:
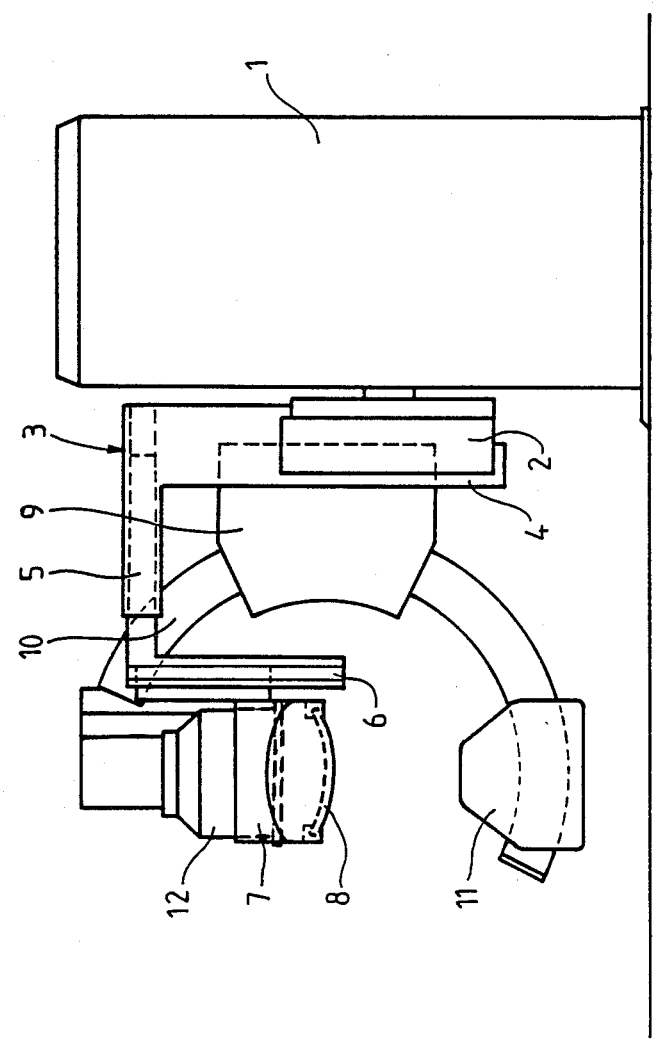
FIG. 1 is a profile view of the radiological device according to the invention.

FIG. 1 presents a radiological device of the pivoting type, comprising a substantially parallelepipedic base 1, in front of which is placed a pivoting carriage 2 which can be displaced vertically by known mechanical means. The carriage 2 carries, at one of its ends perpendicular to its longitudinal axis, a bracket 3 formed of an upright 4 and of a horizontal beam 5. At the free end of the beam 5 of the bracket 3 there is provided an arm 6 which is placed, in the plane formed by the upright 4 and the beam 5, perpendicular to the said beam, the three elements 4, 5, 6 forming a bridge, under which a practitioner may pass. The end of the arm 6 is equipped with an angle member 7 permitting the mounting of a patient support panel 8, the patient support panel being viewed end-on in FIG. 1.

FIG. 1 shows the image of an arch support 9 mounted for rotation and translation on the pivoting carriage 2. The support 9 is equipped with an arch 10, which itself carries an X-ray analysis system composed of an X-ray source 11, opposite which is placed a radiation-receiving tube 12. The source 11 and the tube 12 are placed on either side of the patient when the latter is spread out on the patient support panel 8, in the course of a radiological analysis.

Figure 2:
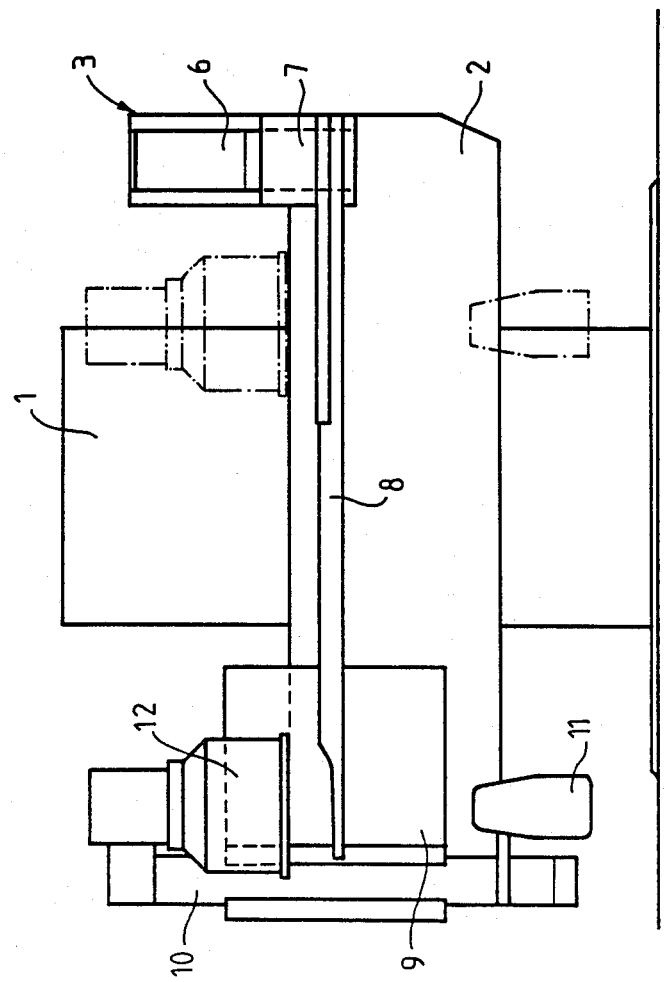
FIG. 2 is a front view of the device of FIG. 1.

FIG. 2 shows the radiological device seen from the front. In front of the base 1 is placed the pivoting carriage 2, at one end of which the bracket 3 is provided, together with the arm 6, the panel support angle member 7 and the patient support panel 8. The arch 10 and its support 9 equipped with the X-ray analysis system located, in the figure, at the other end of the carriage, may be displaced longitudinally in relation to the carriage, the source 11 and the tube 12 being on either side of the patient support panel. The image in thin mixed broken lines indicates another position of the arch in the course of a horizontal displacement of the latter.

By cylindrical rotation of the arch and by pivoting about the axis of rotation of the arch support, it is possible to reverse the position of the source and of the receiving tube, the X-ray source being then displaced above the panel, the analyzer tube being below. The reversal is facilitated by the fact that the patient support panel is mounted so as to overhang and be spaced from the carriage, the reversal being performed by rotational movements of the arch on either side of the patient support panel, without any need to displace the said panel.

I claim:

1. A radiological device of the pivoting type, comprising a base, a pivoting carriage mounted on said base, said pivoting carriage having longitudinally disposed an end region, a patient support panel connected to said carriage at the end region by a patient support panel support means, an arch support means connected to said carriage and equipped with an arch carrying an analysis system comprising an x-ray source and an x-ray receiver, characterized in that said panel support means comprises a bracket forming a solid unit with said pivoting carriage, said bracket being fixed at a lower end to said carriage and comprises a top horizontal beam carrying, at a free end, an arm transverse to said horizontal beam, said arm comprising an angle member connected at a free end, said patient support panel being mounted to said angle member, said bracket and said arm forming a bridge of sufficient size for the passage of practitioner.

2. Radiological device of the pivoting type according to claim 1, characterized in that the beam is a slide in which slides a horizontal sliding member forming a solid unit with the arm.

3. Radiological device of the pivoting type according to claims 1 or 2, characterized in that the arm is equipped with a slideway mounted on the angle member for a displacement of the patient support panel in planes perpendicular to the longitudinal axis of the arm.

* * * * *